(12) United States Patent
Chiang et al.

(10) Patent No.: US 9,669,064 B2
(45) Date of Patent: Jun. 6, 2017

(54) **METHOD FOR ANTI-OXIDATION, INHIBITING ACTIVITY AND/OR EXPRESSION OF MATRIX METALLOPROTEINASE, AND/OR PROMOTING EXPRESSION OF COLLAGEN USING *IXORA PARVIFLORA* LEAF EXTRACT**

(75) Inventors: Hsiu-Mei Chiang, Taichung (TW); Kuo-Ching Wen, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 1293 days.

(21) Appl. No.: 12/856,191

(22) Filed: Aug. 13, 2010

(65) Prior Publication Data
US 2011/0293758 A1 Dec. 1, 2011

(30) Foreign Application Priority Data
May 25, 2010 (TW) ................................ 99116636 A

(51) Int. Cl.
*A61K 36/74* (2006.01)

(52) U.S. Cl.
CPC ................................... *A61K 36/74* (2013.01)

(58) Field of Classification Search
None
See application file for complete search history.

(56) References Cited

FOREIGN PATENT DOCUMENTS

| JP | 2001-163749 A | 6/2001 |
|----|---------------|--------|
| KR | 10-2010-0043717 A | 4/2010 |

OTHER PUBLICATIONS

Poojari et al., Evluation of Antioxidant and Antimicrobial Properties of Ixora brachiata Roxb., 2009, E-J Chem, 6: 625-628.*
Mandal et al., Evaluation of anti-inflammatory potential of *Pavetta indica* Linn. leaf extract (family: Rubiaceae) in rats, 2003, Phytother Res., 17: 817-20.*
2008 http://www.flowersofindia.net/catalog/slides/Small%20Flowered%20Ixora.html.*
2015 http://plants.jstor.org/compilation/ixora.parviflora.*
Fan, Pei-Ching, et al., "Antioxidant activity, MMP inhibition and increase of type I procollagen of Ixora parviflora extract after UV irradiation in human fibroblast", 1 pg., Nov. 28, 2009.
Lalithakumari, et al., "Safety and Toxicological Evaluation of a Novel, Standardized 3-O-Acetyl-11-keto-β-Boswellic Acid (AKBA)-Enriched Boswellia serrata Extract (5-Loxin®)", Toxicology Mechanisms and Methods, 16: 199-226, (2006).
Wilhelmus, Kirk R., "The Draize Eye Test", Survey of Ophthalmology, vol. 45, No. 6, pp. 493-515 (2001).
Fan, et al., "Antioxidant activity, MMP inhibition and increase of type I procollagen of Ixora parviflora extract after UV irradiation in human fibroblast" (abstract only), Nov. 28, 2009, 2 pages.
Official Action issued in the Taiwanese Patent Application No. 099116636 dated Nov. 21, 2012.

* cited by examiner

*Primary Examiner* — Terry A McKelvey
*Assistant Examiner* — Catheryne Chen
(74) *Attorney, Agent, or Firm* — Ping Wang; Andrews Kurth Kenyon LLP

(57) ABSTRACT

A method for anti-oxidation, inhibiting the activity of matrix metalloproteinase (MMP), inhibiting the expression of matrix metalloproteinase, and/or promoting the expression of collagen in a mammal is provided, and the method comprises administrating an effective amount of an *Ixora parviflora* leaf extract to the mammal.

12 Claims, 10 Drawing Sheets

*IPE: *Ixora parviflora* leaf extract

**Dry and fine grind the *Ixora parviflora* leaf extract**
  ↓ added into 30-fold weight methanol
  ↓ soaked for 1 hour
  ↓ ultrasound vibrated for 1 hour

Filtered by a Büchner funnel
  | the residues were further added to a 30-fold methanol and
  ↓ ultrasound vibrated for 1hour

Filtered by a Büchner funnel
  ↓ combine these two filtrates
  ↓ concentrated to dryness under vaccum drying at 30°C to 40°

Store dried extract at -20°C

FIG. 2

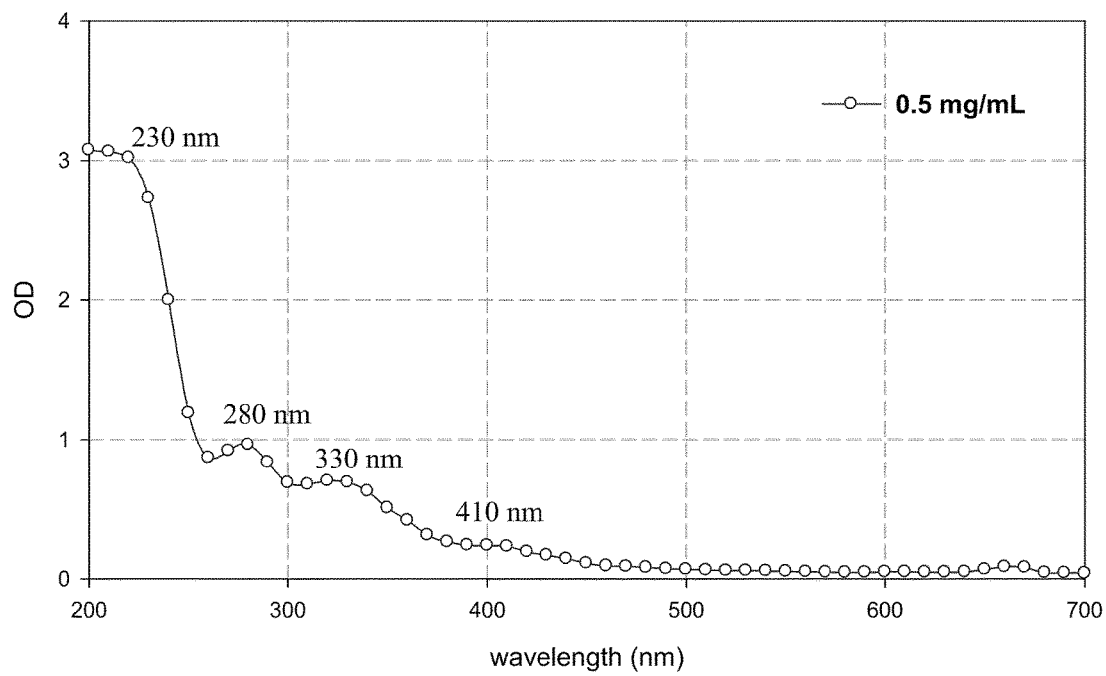

FIG. 3

DC: doxycycline

EGCG: epigallocatechin gallate

METHOD FOR ANTI-OXIDATION, INHIBITING ACTIVITY AND/OR EXPRESSION OF MATRIX METALLOPROTEINASE, AND/OR PROMOTING EXPRESSION OF COLLAGEN USING *IXORA PARVIFLORA* LEAF EXTRACT

RELATED APPLICATION

This application claims the benefit of Taiwan Patent Application No. 099116636, filed on May 25, 2010, the disclosure of which is incorporated herein in its entirety by reference.

BACKGROUND OF THE INVENTION

Field of the Invention

The present invention relates to the uses of an *Ixora parviflora* leaf extract in anti-oxidation, inhibition of the activity of matrix metalloproteinase (MMP), inhibition of the expression of matrix metalloproteinase, and/or the promotion of expression of collagen, especially in the improvement, care, and/or repair of skin.

Descriptions of the Related Art

Natural human aging processes include skin flaccidity, wrinkle formation and skin darkening, which gradually appear with aging. The layers of skin from top to bottom are the epidermis, dermis, and hypodermis. The causes of skin aging can be classified into endogenous and exogenous factors. Endogenous aging is a natural aging process of the human body, including cell apoptosis, hormone decrease, and weakened immunity. The decrease of hormone secretion may slow the skin metabolism and gradually reduce the production of collagen and elastin due to the deterioration of fibroblast function in the dermis. As a result, the connective tissues in the dermis deteriorate, leading to skin flaccidity, and even wrinkling. Furthermore, the deterioration of the connective tissues in the dermis may decrease the water storage function of the skin, leading to skin dryness and water deficiency, etc.

Exogenous aging is caused by extrinsic factors, such as sunshine, pollution, free radicals, and smoking. The main factor that damages the skin most and accelerates the aging of skin is ultraviolet (UV) rays from the sun. Depending on the wavelength, ultraviolet (UV) rays can be classified into long wavelength UV (UVA), medium wavelength UV (UVB), and short wavelength UV (UVC). UV rays that people are most exposed to in daily life are UVA and UVB, which may cause erythema, sunburns, damage to the deoxyribonucleic acid (DNA) in skin cells, abnormality of the skin immune system, and skin cancer. The aging phenomenon caused by UV rays is called "photo-aging," which may increase the amount of matrix metalloproteinase (MMP) in the dermis via the phosphorylation of the mitogen-activated protein kinase (MARK) pathway. Matrix metalloproteinase may decompose collagen to reduce the collagen content in the skin. Furthermore, UV rays may promote the formation of reactive oxygen species (ROS), such as oxygen ions, peroxides, organic and inorganic radicals, etc, and cause denaturing of the collagen and loss of collagen function. Without the support of collagen, the skin becomes flaccid, and cuticula may overgrow, leading to darkened skin.

Currently known animal collagen can be classified approximately into 21 types. Different kinds of collagen exist in different tissues. Out of all collagen in skin tissues, Type I collagen is the most abundant (80% of skin collagen) and has the most functions. Type III collagen comprises about 20% of the skin collagen. Fibroblasts in the dermis mainly produce Type I collagen and Type III collagen for the skin.

As described above, matrix metalloproteinase may decompose collagen to reduce the collagen content in the skin, while reactive oxygen species will cause collagen to lose its function. Thus, if the oxidation reaction of reactive oxygen species or the activity and/or expression of matrix metalloproteinase can be inhibited, then the effects of improving/caring for skin quality can be achieved.

It has been found that the expression of matrix metalloproteinase-1 can be inhibited by ziyuglycoside-I obtained by extracting the roots of *Sanguisorba officinalis* with 70% ethanol. The expression of matrix metalloproteinase-1 can also be inhibited by sumaflavone and amentoflavone obtained by extracting *Selaginella tamariscina* with methanol. However, there is still a need to find components that have better effects of inhibiting the activity of matrix metalloproteinase.

The inventors of the present invention discovered that an *Ixora parviflora* leaf extract has excellent effects of anti-oxidation, inhibiting the activity of matrix metalloproteinase, inhibiting the expression of matrix metalloproteinase, and/or promoting the expression of collagen. Thus, the extract can be used in the improvement, care, and/or repair of skin.

SUMMARY OF THE INVENTION

The primary objective of this invention is to provide a method for anti-oxidation, inhibiting the activity of matrix metalloproteinase (MMP), inhibiting the expression of matrix metalloproteinase, and/or promoting the expression of collagen in a mammal, comprising administrating an effective amount of an *Ixora parviflora* leaf extract to the mammal.

The detailed technology and preferred embodiments implemented for the subject invention are described in the following paragraphs accompanying the appended drawings for people skilled in this field to well appreciate the features of the claimed invention.

BRIEF DESCRIPTION OF THE DRAWINGS

FIG. 2 is a flow chart illustrating the method for preparing the *Ixora parviflora* leaf extract of the present invention;

FIGS. 3 to 5 are UV-VIS spectrograms of the *Ixora parviflora* leaf extract of the present invention;

DESCRIPTION OF THE PREFERRED EMBODIMENT

The present invention relates to a method for anti-oxidation, inhibiting the activity of matrix metalloproteinase (MMP), inhibiting the expression of matrix metalloproteinase, and/or promoting the expression of collagen in a mammal, comprising administrating an effective amount of an *Ixora parviflora* leaf extract to the mammal. The absorption spectroscopy of the *Ixora parviflora* leaf extract includes peaks within the following wavelength ranges: from 210 to 250 nm, from 260 to 290 nm, and from 300 to 350 nm. In one embodiment, the absorption spectroscopy of the *Ixora parviflora* leaf extract includes peaks within the following wavelength ranges: from 220 to 250 nm, from 270 to 290 nm, from 310 to 340 nm, from 390 to 420 nm, and from 650 to 670 nm.

The inventors of the present invention discovered that the *Ixora parviflora* leaf extract of the present invention has effects of inhibiting the activity of matrix metalloproteinase and inhibiting the expression of matrix metalloproteinase, and may prevent or decrease the destruction of collagen. Matrix metalloproteinase can be classified as collagenase, stromelysin, gelatinase, matrilysin, transmembrane type-MMP, etc. In particular, the *Ixora parviflora* leaf extract of the present invention can effectively inhibit the formation (or expression) of matrix metalloproteinase-1 (MMP-1), matrix metalloproteinase-3 (MMP-3), and matrix metalloproteinase-9 (MMP-9). MMP-1 is also called collagenase-1, which belongs to the collagenase family. Other names for MMP-1 include tissue collagenase or fibroblast-type collagenase. MMP-3 is also called stromelysin-1, which belongs to the stromelysin family, substrates of which include fibronectin, laminin, and non-fibrillar collagen. MMP-9 belongs to the gelatinase family, a major substrate of which is Type IV collagen. It is believed, but not limited thereby, that the *Ixora parviflora* leaf extract of the present invention can inhibit the activity and/or expression of matrix metalloproteinase by inhibiting the phosphorylation of mitogen-activated protein kinase (MARK), thus indirectly increasing the formation of collagen.

In addition to the effects of inhibiting the activity and/or expression of matrix metalloproteinase, the *Ixora parviflora* leaf extract of the present invention also has anti-oxidation effects. As described above, the oxidation reaction of reactive oxygen species can cause collagen to denature and lose its function, and thus collagen can no longer support the skin, leading to skin flaccidity and darkening.

Figure 1:
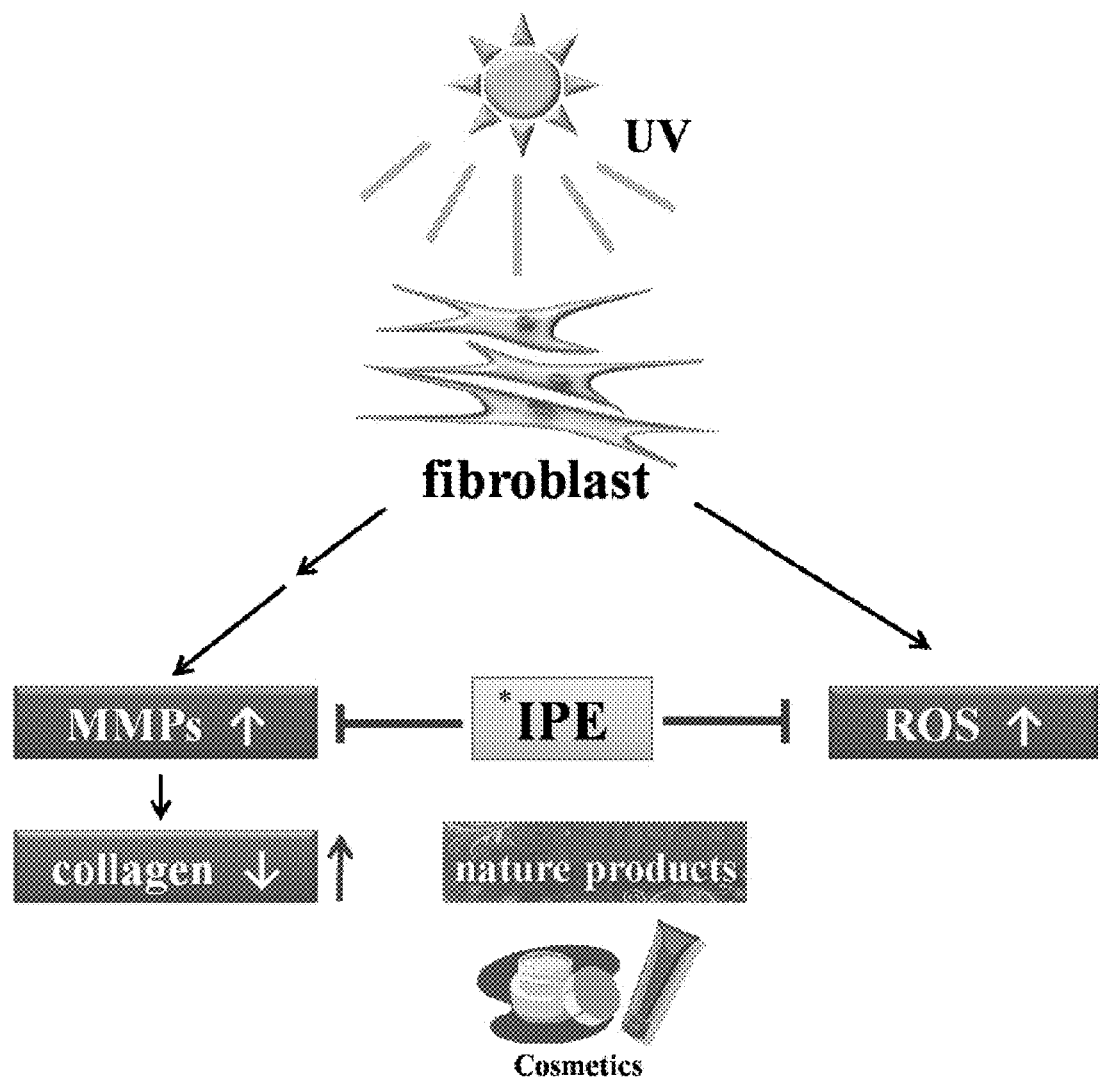
FIG. 1 is a diagram illustrating the mechanism of the *Ixora parviflora* leaf extract of the present invention.

As shown in FIG. 1, because the *Ixora parviflora* leaf extract of the present invention simultaneously has the effects of (1) inhibiting the activity and/or expression of matrix metalloproteinase, and (2) inhibiting the oxidation reaction of reactive oxygen species, and thus greatly reduces collagen decomposition and denaturing in the skin, and may effectively improve, repair, and/or care for skin. For example, the extract may achieve the effects of anti-aging, anti-photoaging, reducing skin wrinkles, improving skin quality, skin flaccidity, promoting wound healing, etc.

The *Ixora parviflora* leaf extract of the present invention can be prepared by a method comprising the following steps: a) extracting *Ixora parviflora* leaves with a polar solvent and collecting the liquid phase; and b) drying the collected liquid optionally. The polar solvent (i.e., extraction solvent) that is commonly used is selected from a group consisting of water, $C_1$-$C_4$ alcohols, and combinations thereof. The polar solvent is preferably selected from a group consisting of water, methanol, ethanol, propanol, butanol, propylene glycol, and combinations thereof. Most preferably, methanol is used as the extraction solvent. The weight ratio of the extraction solvent and *Ixora parviflora* leaves is not a key factor in the present invention, and usually is about 10:1 to about 50:1, and preferably about 20:1 to about 40:1.

In step a), the extraction is carried out for a period of time to achieve the desired extraction efficiency. For example, when methanol is used as the extraction solvent, the extraction time is usually at least 30 minutes, more preferably at least 60 minutes, and most preferably at least 90 minutes. The extraction may be optionally assisted with other appropriate extracting approaches (e.g., ultrasonic vibration, heating, etc.) to increase extraction efficiency. In addition, prior to step b), the extraction in step a) may be optionally repeated one or more times, and all of the liquid phase may be combined to provide a liquid for step b) to separate the active components from the inactive components in *Ixora parviflora* leaves as much as possible to reduce resource waste and benefit the economy.

In general, depending on the application forms of the *Ixora parviflora* leaf extract, a drying step may be optionally carried out to dry the *Ixora parviflora* leaf extract liquid obtained in step a). For example, if the selected extraction solvent is methanol or ethanol, which are not irritating to the skin, and the obtained *Ixora parviflora* leaf extract liquid is to be applied to the skin directly, additional drying for the extract liquid is not needed. However, if the *Ixora parviflora* leaf extract of the present invention is to be applied by oral administration, a drying step (such as freeze drying, concentrating under a vacuum condition, and/or ventilation) can be used to remove organic solvents in the *Ixora parviflora* leaf extract to prevent the organic solvents from harming the body.

In one embodiment of the present invention, *Ixora parviflora* leaves were extracted with methanol and soaked therein to obtain an extract liquid, and the weight ratio of methanol and the *Ixora parviflora* leaves was about 30:1. The extract liquid was then concentrated under a vacuum condition to obtain a dried *Ixora parviflora* leaf extract. The extract is soluble in polar solvents (such as solvents selected from a group consisting of methanol, ethanol, propanol, butanol, propanediol, dimethyl sulfoxide, water, and combinations thereof). When 2 mg of the extract was dissolved in 1 ml methanol, an orange solution can be obtained, the pH value of which was about 4.5 to about 5.0.

The present invention also relates to a medicament for anti-oxidation, inhibiting the activity of matrix metalloproteinase, inhibiting the expression of matrix metalloproteinase, and/or promoting the expression of collagen, comprising an effective amount of the *Ixora parviflora* leaf extract of the present invention. Specifically, the *Ixora parviflora* leaf extract of the present invention can be administrated as a medicament. Based on the effects of anti-oxidation, inhibiting the activity of matrix metalloproteinase, inhibiting the expression of matrix metalloproteinase, and/or promoting the expression of collagen of the medicament of the present invention, the medicament can be particularly used for improving, repairing, and/or caring for the skin.

The medicament of the present invention can be of any suitable form without particular limits. For example, the medicament can be in a form of emulsion, cream or gel for external use, such as a skin care product, cosmetic, etc. The medicament can also be prepared in the form of food for swallowing or drinking, such as health foods, beauty drinks, etc. Furthermore, the medicament can also be of a common pharmaceutical form, such as a tablet, a capsule, a granule, a powder, a fluid extract, a solution, a syrup, a suspension, an emulsion, a tincture, an intravenous injection, a powder injection, a suspension injection, and a powder-suspension injection, etc.

The content of the *Ixora parviflora* leaf extract in the medicament of the present invention may be adjusted according to the age of the treated subject and the purpose of the application (such as reducing skin wrinkles or promoting wound healing). The usage frequency may also be optionally adjusted. For example, when the *Ixora parviflora* leaf extract is used for reducing skin wrinkles, the content of the *Ixora parviflora* leaf extract in the medicament usually ranges from about 0.03 wt % to about 0.4 wt %, and preferably ranges from about 0.05 wt % to about 0.25 wt %, based on the total weight of the medicament. The other components and content thereof are dependent on the final form of the medicament. For instance, when the medicament is prepared as a skin care product, any suitable and appropriate amount of emulsion, perfume, and other active components for improving skin quality may be added therein. When the medicament is prepared as a tablet, an appropriate excipient can be used. In general, any component can be added to the medicament as long as it has no adverse influence on the effects of the *Ixora parviflora* leaf extract.

The detailed technology and preferred embodiments implemented for the subject invention are described in the following paragraphs accompanying the appended drawings for people skilled in this field to well appreciate the features of the claimed invention. However, the scope of the present invention is not limited thereby.

[Preparation of the *Ixora parviflora* Leaf Extract]

Figure 4:
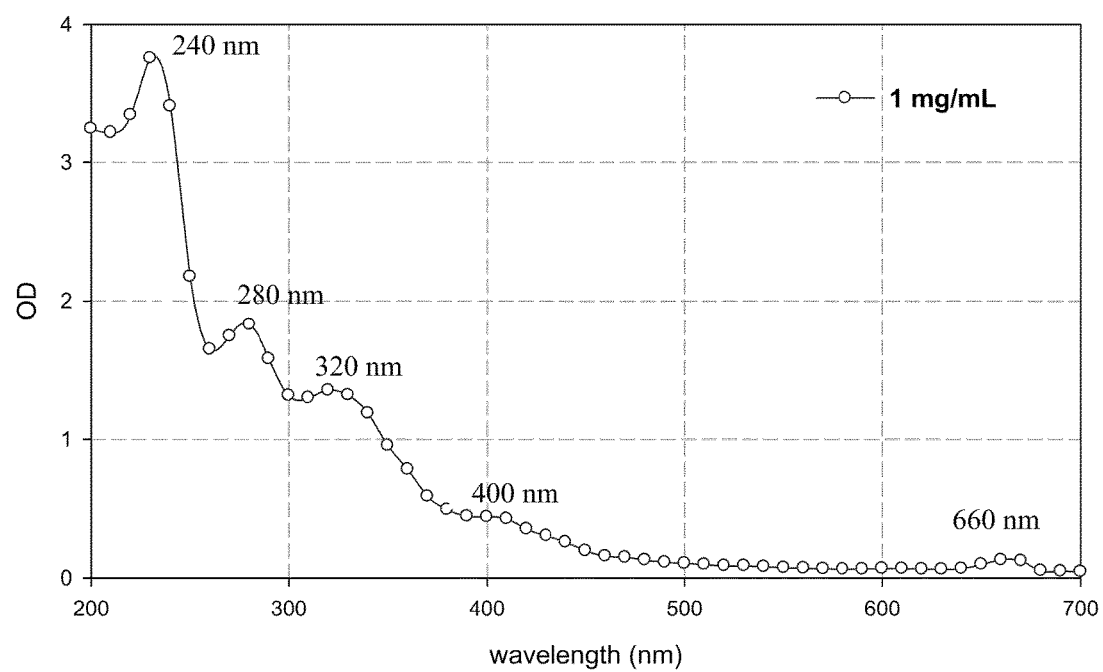
Figure 5:
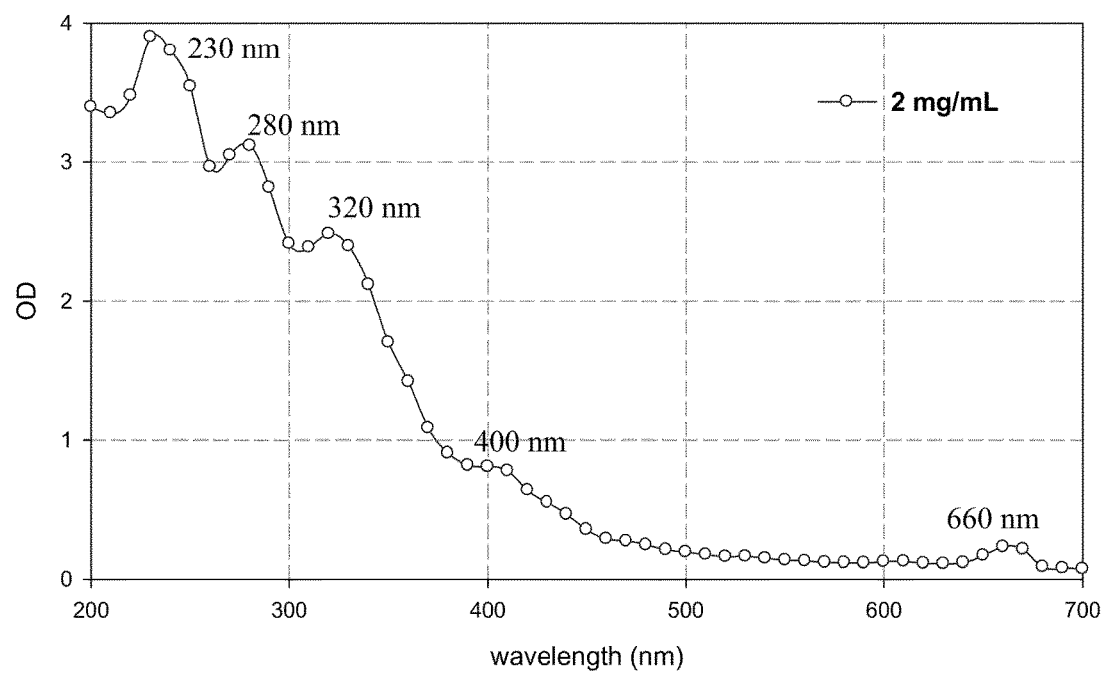

*Ixora parviflora* leaves in the present invention were from the central area of Taiwan. FIG. 2 illustrates a flow chart for preparing the *Ixora parviflora* leaf extract used in the following examples. First, dried *Ixora parviflora* leaves were grinded and added into methanol with a 30-fold weight corresponding to the weight of the leaves. After being soaked and ultrasound vibrated for 1 hour, the leaves were filtered with a Büchner funnel to obtain a filtrate. The filtered residues were added into 30-fold weighted methanol again, and ultrasound vibrated for 1 hour, and then filtered with a Büchner funnel to obtain another filtrate. Then, these two filtrates were combined and concentrated under vacuum drying at the temperature of 30° C. to 40° C., and the *Ixora parviflora* leaf extract of the present invention was obtained, the yield of which was about 13 wt %. An UV-VIS Spectrophotometer (UV-160, Shimadzu) was used to detect the characteristic absorption wavelength of the extract. The UV-VIS absorption spectra are shown in FIGS. 3 to 5.

Example 1

Experiment A. Inhibition Test of Collagenase Activity

An agar gel (agar gel medium) was used in this experiment to evaluate the inhibition effect of the *Ixora parviflora* leaf extract on collagenase.

In an eppendorf tube, 50 μL of a 10-fold diluted buffer solution (prepared by mixing 5 mL of 1 M Tris (pH 7.8), 1 mL of 1 M $CaCl_2$, 3.75 mL of 4M NaCl, and 0.25 mL water), 30 μL of the distilled water, 10 μL of the *Ixora parviflora* leaf extract (125 to 1,000 μg/mL in a 50 vol % propylene glycol aqueous solution), and 10 μL of a bacterial collagenase (100 μg/mL, a multiple-functional collagenase obtained by gene recombination) were added and mixed evenly, and placed at room temperature for 1 hour. The mixed solution (40 μL) was added onto a filter paper on an agar gel medium and placed in an incubator at 37° C. to react for 18 hours. Afterwards, the filter paper was removed, and the medium was stained with a staining agent for 15 minutes, and then destained. A photograph of the medium was taken and analyzed by a TINA software (Prevx community, Germany) to calculate the inhibition rate of the *Ixora parviflora* leaf extract. In the experiment, propylene glycol and doxycycline were used to replace the *Ixora parviflora* leaf extract as a control group and a positive control group, respectively, and distilled water was used to replace collagenase for determining the background value. After the tests were independently carried out for three times, the mean value and standard deviation were calculated with the following formula. The results are shown in Table 1 and FIG. 6.

$$\text{Inhibition Rate (\%)} = \left[\frac{(C-B)}{(A-B)}\right] \times 100$$

A: a solution comprising no collagenase and the extract
B: a solution comprising collagenase, but not the extract
C: a solution comprising collagenase and the extract

TABLE 1

| Group | propylene Glycol | doxycycline (100 μg/mL) | extract (125 μg/mL) | extract (250 μg/mL) | extract (500 μg/mL) | extract (1,000 μg/mL) |
|---|---|---|---|---|---|---|
| Inhibition Rate (%) | 0.0 ± 1.7 | 100.4 ± 0.3 | 84.6 ± 6.2 | 93.0 ± 6.4 | 101.0 ± 4.1 | 103.0 ± 3.4 |

Figure 6:
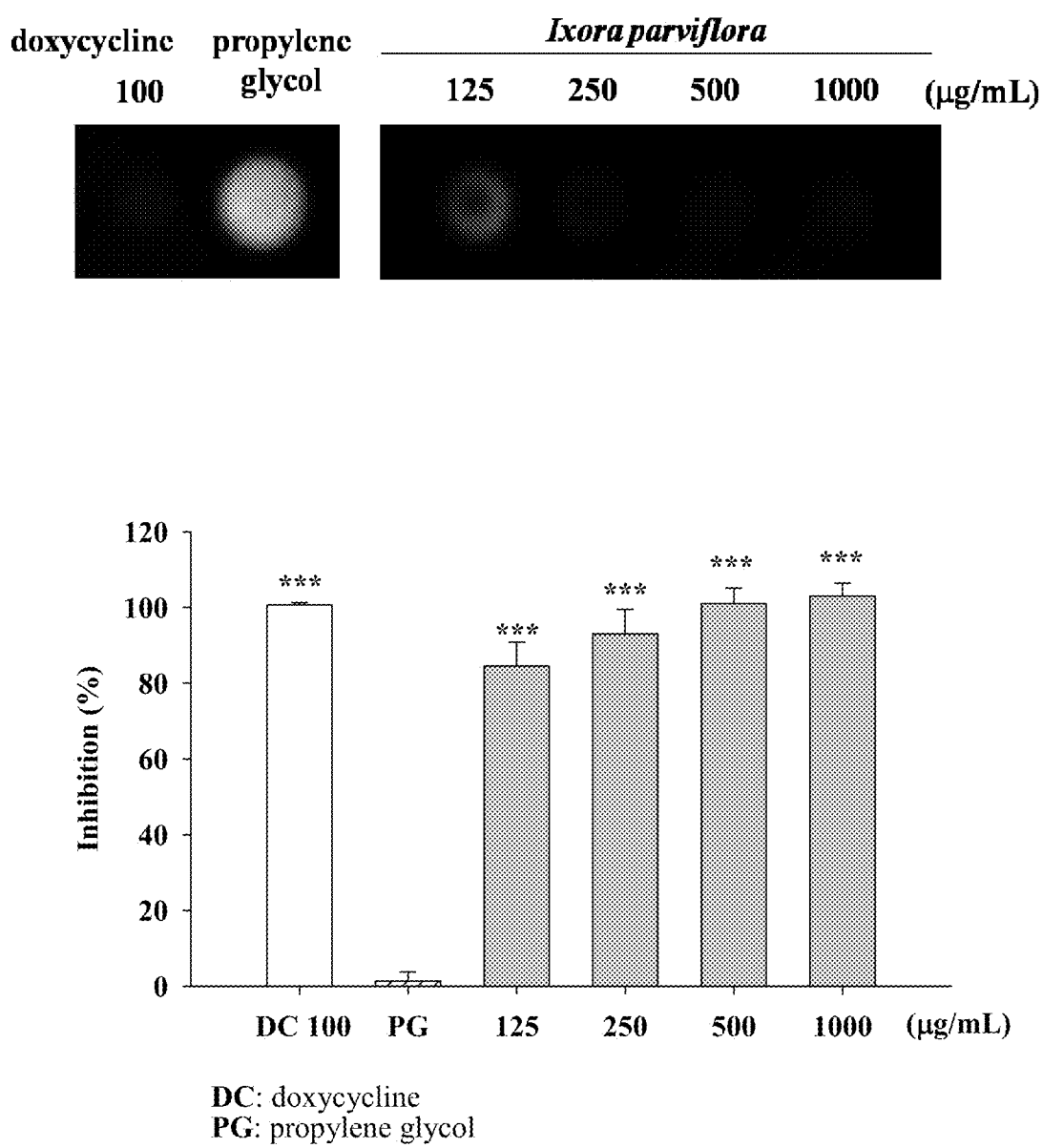
FIG. 6 is a bar diagram showing the inhibition rate of the *Ixora parviflora* leaf extract of the present invention on collagenase.

As shown in Table 1 and FIG. 6, the inhibition rate of doxycycline (100 μg/mL) as the positive control was 100.4±0.3%; the inhibition rate of propylene glycol as a blank was 0.0±1.7%; and the inhibition rate of the *Ixora parviflora* leaf extract was about 80% to about 100%.

This test shows that the *Ixora parviflora* leaf extract of the present invention can inhibit the activity of collagenase effectively.

Experiment B. Concentration-Dependent Inhibition Test of Collagenase Activity

To further confirm the inhibition effects of the *Ixora parviflora* leaf extract on collagenase, the extract was diluted to various concentrations (10 to 500 μg/mL).

In an eppendorf tube, 132 μL of the distilled water, 22 μL of a 10-fold diluted buffer solution (prepared by mixing 5 mL of 1 M Tris (pH 7.8), 1 mL of 1 M $CaCl_2$, 3.75 mL of 4 M NaCl, and 0.25 mL water), 22 μL of the *Ixora parviflora* leaf extract (10 to 500 μg/mL), 22 μL of a bacterial collagenase (100 mg/mL), and 22 μL of a fluorogenic substrate (fluorogenic peptide substrate I of collagenase) solution were added and mixed evenly, and placed in an incubator at 37° C. to react for 20 hours. Then, 200 μL of the reacted solution was placed into a 96-well microplate. The fluorescent strength of the solution was tested under 320 nm exciting light and 450 nm radiation light by an enzyme immunoassay instrument. In the experiment, distilled water and doxycycline were used to replace the *Ixora parviflora* leaf extract as a control group and a positive control group, respectively, and collagenase and fluorogenic substrate were replaced by distilled water for determining the background value. After the tests were independently carried out for three times, the mean value and standard deviation were calculated with the following formula. The results are shown in Table 2 and FIG. 7.

$$\text{Inhibition Rate (\%)} = \left[\frac{\text{Absorption value of the control group} - \text{Absorption value of the experiment group}}{\text{Absorption value of the control group}}\right] \times 100$$

TABLE 2

| Group | doxycycline (100 µg/mL) | extract (10 µg/ml) | extract (50 µg/ml) | extract (100 µg/ml) | extract (500 µg/ml) |
|---|---|---|---|---|---|
| Inhibition Rate (%) | 100 ± 0.0 | 37.8 ± 2.6 | 70.9 ± 2.2 | 83.4 ± 2.3 | 97.7 ± 0.3 |

Figure 7:
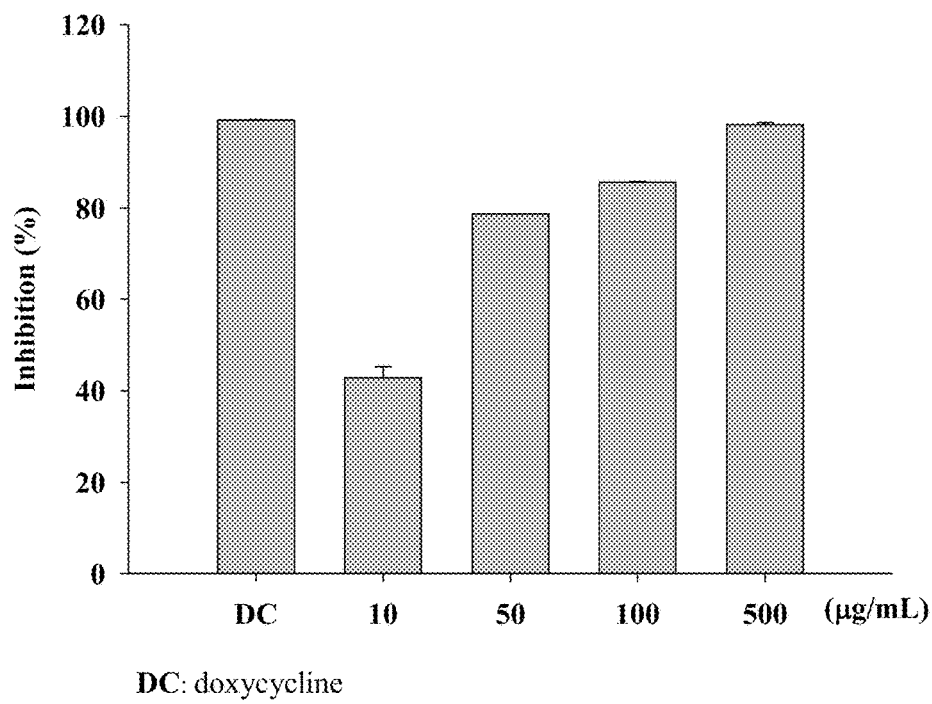
FIG. 7 is a bar diagram showing the inhibition rate of the *Ixora parviflora* leaf extract of the present invention on collagenase.

As shown in Table 2 and FIG. 7, the inhibition effect of the *Ixora parviflora* leaf extract was concentration-dependent and it had an excellent inhibition effect on collagenase.

Example 2

Experiment C. Inhibition Test of Matrix Metalloproteinase Expression

A total of $5 \times 10^5$ fibroblast Hs68 (human foreskin fibroblast, Bioresource Collection and Research Center (BCRC) number:60038, purchased from Food Industry Research and Development Institute (FIRDI)) was counted and cultivated in a culture medium (90% Dulbecco's modified Eagle's medium adjusted with 4 mM of L-glutamine, containing 1.5 g/L $NaHCO_3$, 4.5 g/L glucose, and 10% heat-inactivated fetal bovine serum) with a diameter of 10 cm. After the fibroblast Hs68 grew to a density of 80%, the culture solution was removed, and the cells were rinsed with 5 mL of a phosphate buffer saline (PBS) solution once. Then, 3 mL of a phenol red-free culture solution containing the *Ixora parviflora* leaf extract with different concentrations (0 to 50 mg/mL) was added into the culture medium, and was reacted for 1 hour. The cells were placed under ultraviolet light (80 $mJ/cm^2$, Ultraviolet B (UVB)) for irradiation. Afterwards, 7 mL of a phenol red-free culture solution containing the *Ixora parviflora* leaf extract with different concentrations (0 to 50 mg/mL) was further added into the culture medium, and the cells were cultured in an incubator at 37° C. containing 5 vol % carbon dioxide for 48 hours, and then the cells were collected.

A lysing buffer solution (comprising 100 mM $Na_3VO_4$, 100 mg/mL Phenylmethanesulfonyl fluoride (PMSFL), 20 mg/mL Leupeptin, 50 mM Tris-HCl with pH 7.4, 37.5 mM NaCl, 250 mM DL-dithiothreitol, 3 mM of Sodium deoxycholate, 1 mM EDTA, 0.1% SDS, and 1% Igepal™ CA-630 (purchased from Sigma-Aldrich)) was used to treat the collected cells. An additional physical vibration was applied to break the cell membranes, and cell organelles and fragments were precipitated by a centrifuge. The supernatant containing cytoplasm proteins were collected. The collected proteins were separated by SDS-PAGE gel electrophoresis and were transferred to a membrane by western blotting. Based on the antigen-antibody principle, antibodies were used to detect target proteins, including Type I pro-collagen, MMP-1, MMP-3, MMP-9, and β-actin. Using luminescence imaging technology with an associated analysis software and LAS-4000 (FUJIFILM) to record the image, and a quantitative analysis was carried out by multi Gauge V2.2 (Steware Technology Inc.) to test the variation of the expression of target proteins.

Figure 8:
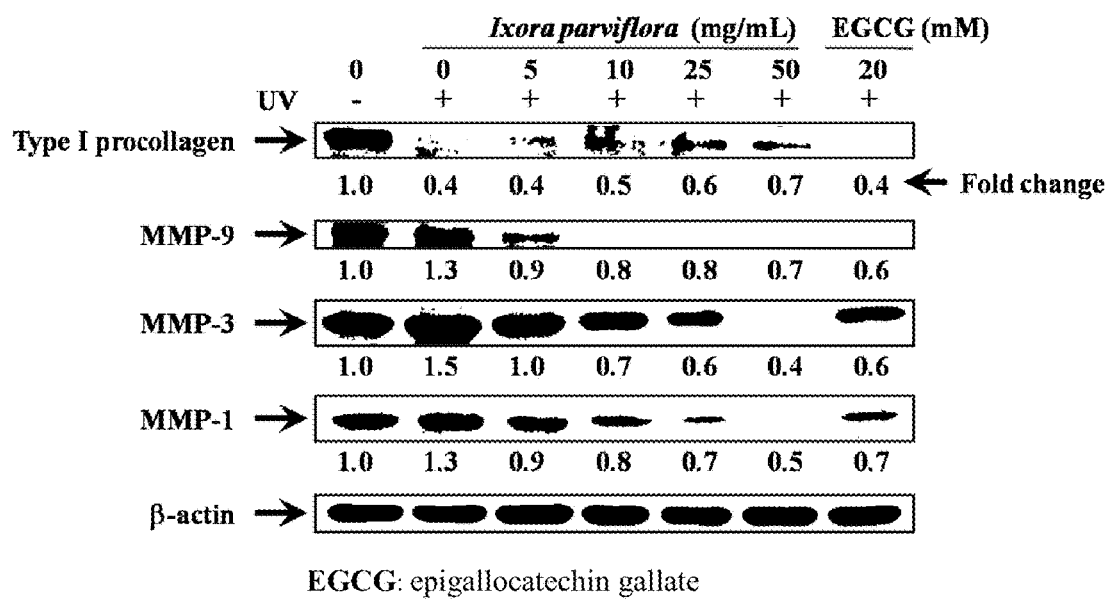
FIG. 8 is a protein electrophoresis picture of matrix metalloproteinase (MMP-1, MMP-3, and MMP-9) and Type I pro-collagen in fibroblast Hs68.

As shown in FIG. 8, the expression amount of MMP-1, MMP-3, and MMP-9 in the fibroblasts increased to 1.3-fold, 1.5-fold, and 1.3-fold, respectively. After UV light radiation, the fibroblasts were further treated by the *Ixora parviflora* leaf extract, and under the concentration of 25 mg/mL of the extract, the expression of MMP-1 decreased significantly from 1.3-fold to 0.7-fold, the expression of MMP-3 decreased from 1.5-fold to 0.6-fold, and the expression of MMP-9 decreased from 1.3-fold to 0.8-fold. In addition, after UV light radiation, the expression of Type I pro-collagen decreased to 0.4-fold, but after the fibroblasts were treated by the *Ixora parviflora* leaf extract under the concentration of 50 mg/mL, the expression of Type I pro-collagen increased to 0.7-fold.

Example 3

Experiment D. Anti-Oxidation Tests—Free Radicals Removal Test

DPPH (1,1-diphenyl-2-picrylhydrazyl) was used as the source of free radicals to test the ability of the *Ixora parviflora* leaf extract to remove free radicals. A 100 µL of the *Ixora parviflora* leaf extract with different concentrations (50 to 1000 µg/mL) and a 100 µL of a DPPH solution (200 µM) dissolved in methanol were added in a 96-well microplate, and were mixed evenly and placed under room temperature away from light for 30 minutes. The absorbance of the mixture was determined by an enzyme immunoassay instrument with a wavelength of 517 nm. In this test, the extract was replaced by 50 vol % propylene glycol as the control group, and ascorbic acid was used as a positive control group, and DPPH was replaced by methanol for determining the background value. The ability of the *Ixora parviflora* leaf extract to remove free radicals was calculated by the following formula. The results are shown in Table 3 and FIG. 9.

$$\text{Clearance efficiency (\%)} = \left[\frac{\text{Absorption value of the control group} - \text{Absorption value of the experiment group}}{\text{Absorption value of the control group}}\right] \times 100$$

TABLE 3

| Concentration | The *Ixora parviflora* leaf extract | | | |
|---|---|---|---|---|
| (µg/mL) | 50 | 100 | 500 | 1000 |
| Clearance Efficiency (%) | 66.1 ± 1.0 | 89.3 ± 1.7 | 96.3 ± 0.1 | 96.7 ± 0.5 |

Figure 9:
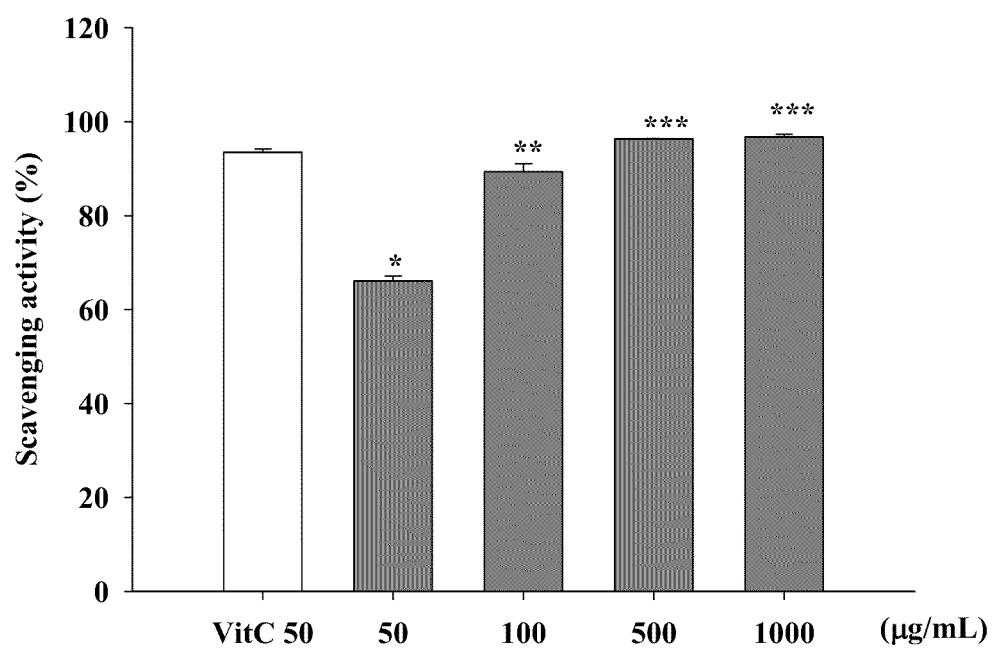
FIG. 9 is a bar diagram showing the clearance efficiency of the *Ixora parviflora* leaf extract of the present invention for DPPH free radicals.

As shown in Table 3 and FIG. 9, the $IC_{50}$ value of the *Ixora parviflora* leaf extract to remove half of DPPH free radicals was 23.8 µg/mL, which shows that the extract can effectively remove free radicals, and thus has an anti-oxidation ability.

Experiment E. Anti-Oxidation Tests—Free Radicals Inhibition Tests

AAPH (2,2'-Azobis(2-methylpropionamidine)dihydrochloride) was used as the free radical source and rat red blood cells were used to mimic a biomembrane to examine the ability of the *Ixora parviflora* leaf extract to protect biomembrane from damage of free radicals. Firstly, 100 µL of the *Ixora parviflora* leaf extract with different concentrations (0 to 500 µg/mL) was added into a solution containing 100 µL of a 20% red blood cell suspension and a 100 µL of an AAPH solution (300 mM), and mixed gently with a vibrator and reacted under 37° C. The samples were taken at a reaction time of 1, 2, 3, and 4 hours (number of sample=3), and 300 µL of a phosphate buffer solution was added therein to terminate the reaction. Then, the samples were centrifuged at 3000 g for 2 minutes. A 200 µL of the supernatant was placed in a 96-well microplate, and the absorbance thereof was tested by an enzyme immunoassay instrument with a wavelength of 540 nm. The *Ixora parviflora* extract was replaced by the phosphate buffer solution as a control group, and the 20% red blood cell suspension was replaced by the phosphate buffer solution for determining the background value. The ability of the *Ixora parviflora* leaf extract to inhibit free radicals was calculated by the following formula, and the results are shown in Table 4, FIG. 10A, and FIG. 10B.

$$\text{Inhibition Rate (\%)} = \left[\frac{\text{Absorption value of the control group} - \text{Absorption value of the experiment group}}{\text{Absorption value of the control group}}\right] \times 100$$

concentration of the *Ixora parviflora* leaf extract increased, the inhibition rate also increased, which demonstrated that the anti-free radical activity of the *Ixora parviflora* leaf extract was concentration dependent. The results in this experiment demonstrate that the *Ixora parviflora* leaf extract can effectively inhibit the activity of free radicals, and hence has the anti-oxidation ability.

Example 4

Experiment F. Cytotoxicity Test

The cytotoxicity of the *Ixora parviflora* leaf extract was observed with an MTT (3-(4,5-dimethylthiazol-2-yl)-2,5-diphenyl tetrazolium bromide) assay. First, 50 µL of various concentrations (0 to 500 µg/mL, in a 50 vol % propylene glycol aqueous solution) of the *Ixora parviflora* leaf extract was added into a 96-well culture plate that comprised fibroblast Hs68 ($10^4$ cells/well). After the cells were incubated in an incubator comprising 5 vol % carbon dioxide at 37° C. for 24 hours, 15 µL of a MTT solution (5 mg/mL, in PBS) was added into the well, and the fibroblasts were further incubated for 3 hours. Then, 75 µL, of a sodium dodecyl sulfate (SDS) solution (10% SDS, in 0.01 N HCl) was added into the culture plate, and the absorbance of each well was measured by an enzyme immunoassay instrument with a wavelength of 570 nm after 24 hours. Finally, the cell survival rate was calculated by the following formula, and the cytotoxicity of the extract was observed. The results are shown in Table 5 and FIG. 11.

TABLE 4

| Time | Extract Concentration (µg/mL) (%) | | | | |
|---|---|---|---|---|---|
| (hour) | 0 | 10 | 50 | 100 | 500 |
| 1 | 0.0 ± 9.5 | 47.9 ± 14.1 | 74.2 ± 4.7 | 79.5 ± 8.0 | 100.7 ± 2.3 |
| 2 | 0.0 ± 22.2 | 75.9 ± 3.3 | 83.9 ± 4.6 | 88.4 ± 1.0 | 95.0 ± 3.3 |
| 3 | 0.0 ± 10.0 | 54.6 ± 4.7 | 67.5 ± 2.3 | 71.2 ± 1.9 | 90.0 ± 2.4 |
| 4 | 0.0 ± 12.5 | 18.7 ± 10.7 | 37.0 ± 10.9 | 52.8 ± 2.6 | 89.4 ± 1.8 |

Figure 10A:
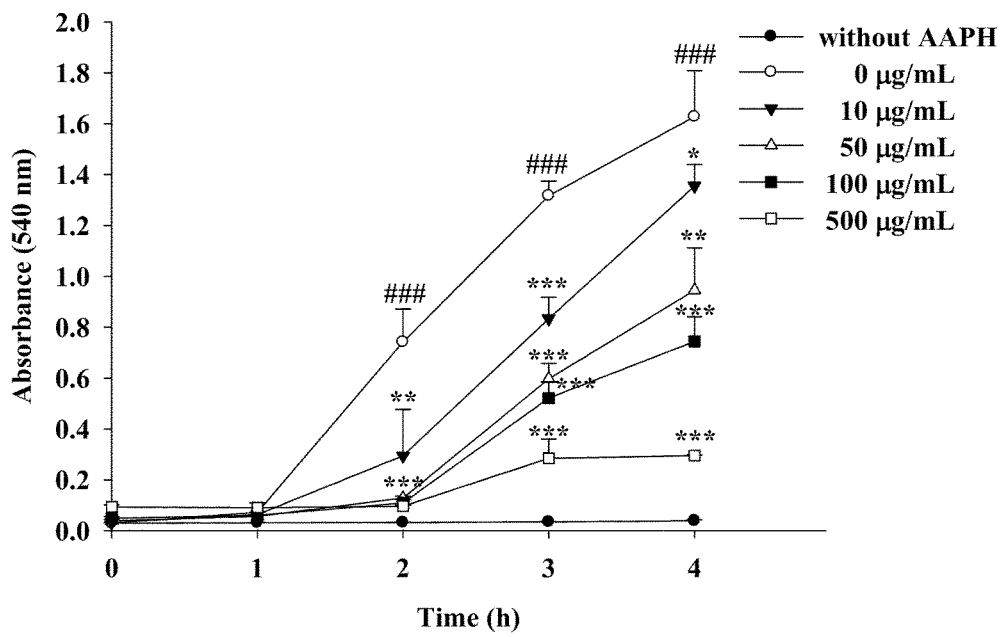
FIGS. 10A and 10B are curve diagrams showing the inhibition rate of the *Ixora parviflora* leaf extract of the present invention on AAPH free radicals.
Figure 10B:
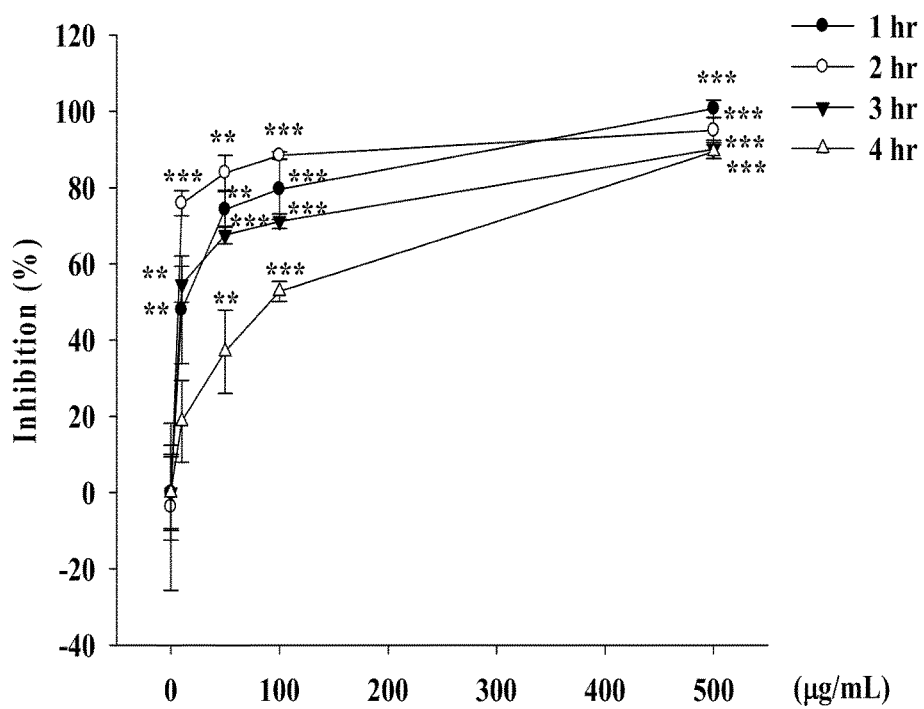

In FIG. 10A, it showed that red blood cells did not undergo haemolysis during reaction (1, 2, 3, and 4 hours) in the samples with no AAPH. However, the samples comprising AAPH showed haemolysis after being placed in an incubator at 37° C. for 2 hours, and haemolysis increased as the reaction interval time increased, which showed that the induction of red cell haemolysis by AAPH was time dependent. Different concentrations of the *Ixora parviflora* leaf extract were added into the samples, and it showed significant inhibition of haemolysis with a concentration of 10 µg/mL after 2 hours. The inhibition rate for inhibition of AAPH free radicals to induce haemolysis of red blood cells is 75.9±3.3%. Furthermore, as shown in FIG. 10B, when the $$\text{Cellular Survival Rate (\%)} = \left[\frac{\text{Absorption value of the experiment group}}{\text{Absorption value of the control group}}\right] \times 100$$

TABLE 5

| | Extract Concentration (µg/mL) | | | | | |
|---|---|---|---|---|---|---|
| | 0 | 5 | 10 | 50 | 100 | 500 |
| Cell Survival Rate (100%) | 100.1 ± 4.4 | 100.4 ± 3.5 | 101.0 ± 1.4 | 98.3 ± 0.4 | 96.6 ± 1.0 | 94.6 ± 1.8 |

Figure 11:
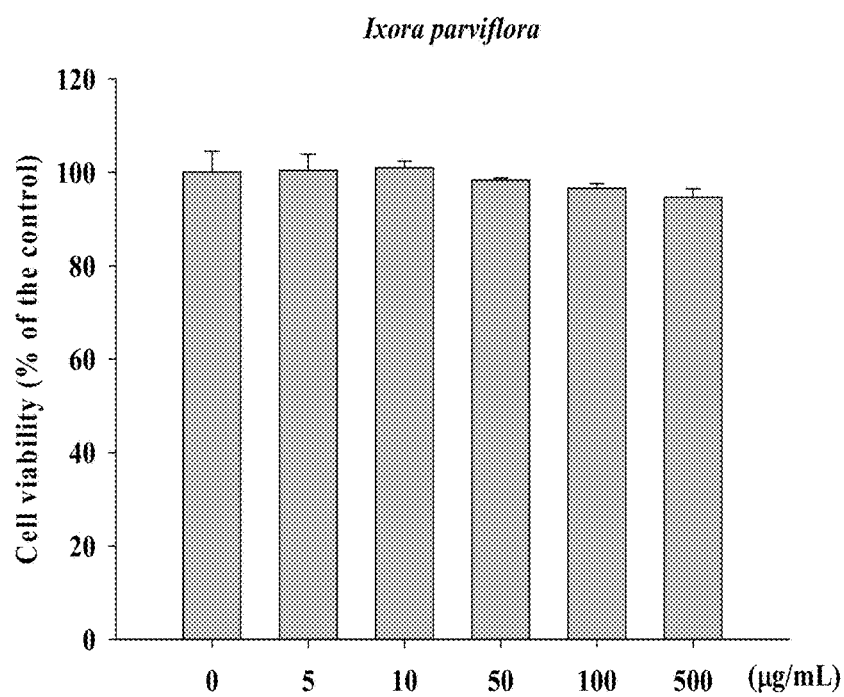
FIG. 11 is a bar diagram showing the cell viability of fibroblast Hs68.

As shown in Table 5 and FIG. 11, after the fibroblasts were treated with 5 to 500 µg/mL of the *Ixora parviflora* leaf extract, even under a high concentration of 500 µg/mL, the *Ixora parviflora* leaf extract showed no cytotoxicity. Thus, the test demonstrated that the *Ixora parviflora* leaf extract is not toxic to the cell or the body.

Experiment G

Primary Skin Irritation Test

First, 0.1 g (low dose) and 0.5 g (high dose) of the *Ixora parviflora* leaf extract were dissolved in 1 mL of a saline solution, respectively. Then, a New Zealand white rabbit (a total of four rabbits were tested in this experiment) was fixed, and the fur on the back of the rabbit was removed. Six squares (each square for 2.5 cm×2.5 cm) for application of the *Ixora parviflora* leaf extract were painted with a color pen on the back of the rabbit. Four parallel lines were made with a sterile needle within one of the squares on the skin of the rabbit to damage the cuticular layer but without bleeding (not to damage the cuticular layer for comparison). The low dose and high dose of the *Ixora parviflora* leaf extract were applied to the skin of the rabbit within the squares uniformly, respectively. After 24 hours, the skin of rabbit was wiped with a saline solution to remove the *Ixora parviflora* leaf extract, and the irritation level was observed at 24 hours and 72 hours. A Primary Irritation Index (PII) was acquired according to the Draize method (see Kirk et al., Therapeutic Reviews, *Survey of Ophthalmology*, vol 45, No. 6, 2001, which is entirely incorporated hereinto as a reference). The observation time would be extended if the *Ixora parviflora* leaf extract irritated the skin of the rabbit. The standards for evaluating the irritation level and Primary Irritation Index are shown in Table 6.

The statistical analysis in this test was based on ANOVA (analysis of variance) and Student's t-test, and if p<0.05, the data is statistically different. Each experiment was carried out for more than three times, and the results of the experiments are represented as a value of mean±standard deviation. The results are shown in Table 7A, Table 7B, and FIG. 12.

TABLE 6

Standard for scoring Primary Irritation Index

| SKIN REACTIONS | SCORE |
| --- | --- |
| Erythema and Eschar Formation | |
| No erythema | 0 |
| Very slight erythema (barely noticeable) | 1 |
| Well-defined erythema | 2 |
| Moderate to severe erythema | 3 |
| Severe erythema (beet redness) to slight eschar formation (injuries in depth) | 4 |
| Edema formation | |
| No edema | 0 |
| Very slight edema(barely noticeable) | 1 |
| Slight edema(edges of area well defined by definite raising) | 2 |
| Moderate edema (raised approximately 1 mm) | 3 |
| Severe edema (raised more than 1 mm and extended beyond the area of exposure) | 4 |

Maximum Irritation Score: 8

| Primary Irritation Index (PII) | Evaluation |
| --- | --- |
| 0 | No irritation |
| 0.04~0.99 | Irritation barely noticeable |
| 1.00~1.99 | Slight irritation |
| 2.00~2.99 | Mild irritation |
| 3.00~5.99 | Moderate irritation |
| 6.00~8.00 | Severe irritation |

TABLE 7A

Primary Irritation Index of a low dose (0.1 g) of the *Ixora parviflora* leaf extract

| Time | Rabbit No. | | | | | | | | Mean ± standard deviation | |
| --- | --- | --- | --- | --- | --- | --- | --- | --- | --- | --- |
| | 1 | | 2 | | 3 | | 4 | | | |
| (hr) | *intact | *abraded | intact | abraded | intact | abraded | intact | abraded | intact | abraded |
| 24 (Control) | 0 | 0 | 0 | 0 | 0 | 0 | 0 | 0 | 0.00 ± 0.00 | 0.00 ± 0.00 |
| 72 (Control) | 0 | 0 | 0 | 0 | 0 | 0 | 0 | 0 | 0.00 ± 0.00 | 0.00 ± 0.00 |
| 24 | 0 | 0 | 0 | 0 | 0 | 0 | 0 | 0 | 0.00 ± 0.00 | 0.00 ± 0.00 |
| 72 | 0 | 0 | 0 | 0 | 0 | 0 | 0 | 0 | 0.00 ± 0.00 | 0.00 ± 0.00 |

*intact: evaluation of irritation to intact skin; abraded: evaluation of irritation of damaged skin

TABLE 7B

Primary Irritation Index of a high dose (0.5 g) of the *Ixora parviflora* leaf extract

| Time | Rabbit No. | | | | | | | | Mean ± standard deviation | |
| --- | --- | --- | --- | --- | --- | --- | --- | --- | --- | --- |
| | 1 | | 2 | | 3 | | 4 | | | |
| (hr) | *intact | *abraded | intact | abraded | intact | abraded | intact | abraded | intact | abraded |
| 24 (Control) | 0 | 0 | 0 | 0 | 0 | 0 | 0 | 0 | 0.00 ± 0.00 | 0.00 ± 0.00 |
| 72 (Control) | 0 | 0 | 0 | 0 | 0 | 0 | 0 | 0 | 0.00 ± 0.00 | 0.00 ± 0.00 |

TABLE 7B-continued

Primary Irritation Index of a high dose (0.5 g) of the *Ixora parviflora* leaf extract

| Time (hr) | Rabbit No. | | | | | | | | Mean ± standard deviation | |
|---|---|---|---|---|---|---|---|---|---|---|
| | 1 | | 2 | | 3 | | 4 | | | |
| | *intact | *abraded | intact | abraded | intact | abraded | intact | abraded | intact | abraded |
| 24 | 0 | 0 | 0 | 0 | 0 | 0 | 0 | 0 | 0.00 ± 0.00 | 0.50 ± 0.50 |
| 72 | 0 | 0 | 0 | 0 | 0 | 0 | 0 | 0 | 0.00 ± 0.00 | 0.50 ± 0.50 |

Figure 12:
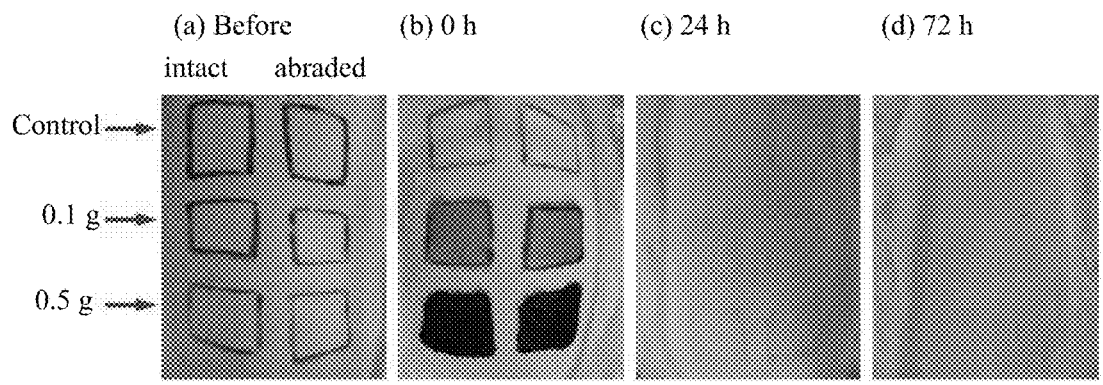
FIG. 12 is a picture showing the skin variation of the rabbits in the primary skin irritation test.

*intact: evaluation of irritation to intact skin; abraded: evaluation of the irritation to damaged skin As shown in FIG. 12, Table 7A, and Table 7B, after 24 hours and 72 hours, the *Ixora parviflora* leaf extract did not produce irritation regardless of low dose (0.1 g) or high dose (0.5 g). The irritation index of the extract is 0.0, categorizing the value in the irritation range of "no-irritation".

This test shows that the *Ixora parviflora* leaf extract of the present invention is not irritating to the skin.

Experiment H. Eye Irritation Test

After 600 μg of the *Ixora parviflora* leaf extract was dissolved in 1 mL of a saline solution and centrifuged at 6,000 rpm for 5 minutes, the supernatant was collected as a test sample. The sample (600 μg/mL (100 μL)) was dropped into the conjunctiva sac of one eye of a New Zealand White rabbit (a total of four rabbits was tested in this experiment), whereas the other eye was not administered with the sample to serve as a control group. The eyes of the rabbit were closed lightly. The influence of the *Ixora parviflora* leaf extract on the eye of the rabbit was observed at 1, 5, 15, 30 minutes, and 1, 2, 24, and 48 hours, etc., and an irritation level was determined according to the Draize method. The observation time would be extended if the *Ixora parviflora* leaf extract generates irritation to the eye of the rabbit. The irritation level is scaled based on the Lalithakumari's Standard of Eye Irritation Level Index, which is shown in Table 8A and Table 8B (see Lalithakumari et al., Safety and Toxicological Evaluation of a Novel, Standardized 3-O-Acetyl-11-keto-β-Boswellic Acid (AKBA)-Enriched *Boswellia serrata* Extract (5-Loxin®), *Toxicology Mechanisms and Methods,* 16:199-226, 2006, which is entirely incorporated hereinto as a reference). The statistical analysis in this test was based on ANOVA and Student's t-test, and if $p<0.05$, the data is significantly different. Each experiment was carried out more than three times, and the results are represented as a value of mean±standard deviation. The results are shown in Table 9 and FIG. 13.

TABLE 8A

Standard for scoring eye irritation*

| Assessment | Score |
|---|---|
| CORNEA | |
| A. Opacity | |
| Scattered or diffuse area; details of iris clearly visible | 1 |
| Easily discernible translucent area, details of iris slightly obscured | 2 |
| Opalescent areas, no details of iris visible, size of pupil barely discernible Opaque; iris invisible | 3 |
| | 4 |
| B. Opaque area of cornea involved | |
| One quarter (or less) but not zero | 1 |
| Greater than one quarter, less than one half | 2 |

TABLE 8A-continued

Standard for scoring eye irritation*

| Assessment | Score |
|---|---|
| Greater than one half, less than three quarters | 3 |
| Greater than three quarters, up to whole area | 4 |
| | Score = A × B × 5 (range, 0 to 80) |
| IRIS | |
| Folds above normal, congestion, swelling, and/or circumcorneal injection; iris still reacting to light (sluggish reaction is positive) | 1 |
| No reaction to light, hemorrhage, and/or gross destruction | 2 |
| | Score = A × 5 (range, 0 to 10) |
| CONJUNCTIVAE | |
| A. Redness of palpebral conjunctiva | |
| Vessels definitely injected above normal | 1 |
| More diffuse, deeper crimson red, individual vessels not easily discernible | 2 |
| Diffuse beefy red | 3 |
| B. Conjunctivae edema | |
| Any swelling above normal (includes nictiating membranes) | 1 |
| Obvious swelling with partial eversion of the lids | 2 |
| Swelling with lids about half closed | 3 |
| Swelling with eyelid about half closed to completely closed | 4 |
| C. Discharge | |
| Discharge is above normal amount | 1 |
| Discharge with moistening of the lids and hairs just adjacent to the lids | 2 |
| Discharge with moistening of the lids and considerable area around the eye | 3 |
| Total score = Sum of all scores obtained for the cornea, iris, and conjunctivae | Score = (A + B + C) × 2 (range, 0 to 20) |

*Kirk et al., Therapeutic Reviews, *Survey of Ophthalmology,* vol 45, No. 6, 2001

TABLE 8B

Eye irritation level

| Level | Primary Irritation Index (PII) |
|---|---|
| No irritation | 0 |
| Slight irritation | 0.1~15.0 |
| Mild irritation | 15.0~25.0 |
| Moderate irritation | 25.0~50.0 |
| Strong irritation | 50.0~80.0 |
| Severe irritation | 80.0~110 |

TABLE 9

Eye irritation score of the *Ixora parviflora* leaf extract

| Time | Rabbit No. | | | | Mean ± standard deviation | Draize scale for scoring eye irritation |
|---|---|---|---|---|---|---|
| | 1 | 2 | 3 | 4 | | |
| 1 minutes | 0 | 4 | 0 | 2 | 1.50 ± 1.91 | 1.2 |
| 5 minutes | 0 | 0 | 2 | 2 | 1.00 ± 1.15 | |
| 15 minutes | 0 | 2 | 2 | 2 | 1.50 ± 1.00 | |
| 30 minutes | 0 | 2 | 2 | 2 | 1.50 ± 1.00 | |
| 1 hour | 2 | 2 | 2 | 2 | 2.00 ± 0.00 | |
| 24 hours | 2 | 2 | 2 | 2 | 2.00 ± 0.00 | |
| 48 hours | 0 | 0 | 0 | 0 | 0.00 ± 0..00 | |
| 72 hours | 0 | 0 | 0 | 0 | 0.00 ± 0.00 | |

Figure 13:
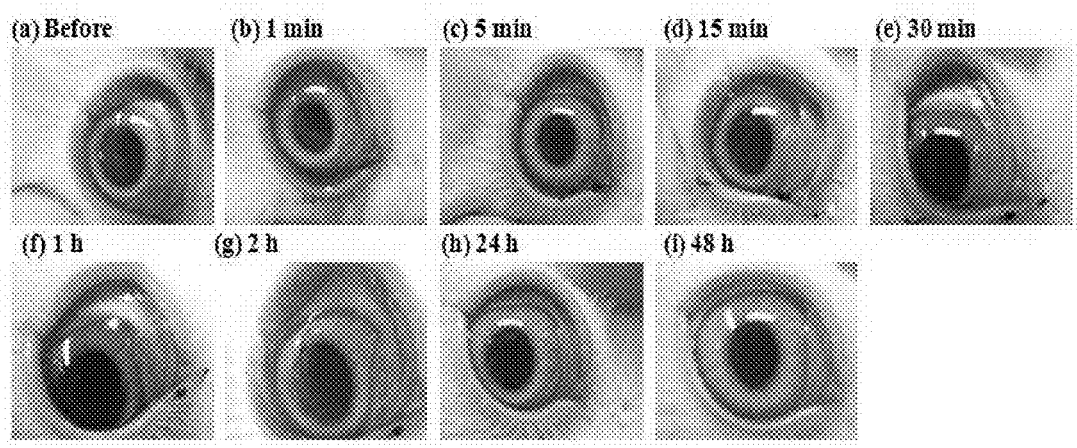
FIG. 13 is a picture showing the eye variation of rabbits in the eye irritation test.

As shown in FIG. 13, compared to the control group, during the experiment, the slight congestion of the conjunctiva of two rabbits administrated with the *Ixora parviflora* leaf extract was observed after 1 minute. In addition, one of the rabbits discharged tears, where the irritation was each scored as 2 and 4, respectively. At time of 5 minutes, the conjunctiva of two rabbits had slight swelling where they were each scored as 2, respectively. At time of 15 and 30 minutes, the conjunctiva of three rabbits had slight swelling where they were each scored as 2, and at 1 and 2 hours, the conjunctiva of four rabbits had slight swelling where they were each scored as 2. At time of 24 hours and 48 hours, the right eyes of the rabbits were the same as the control group where they were scored as 0. As shown in Table 9, the total eye irritation score was 1.2, belonging to the level of practically "no irritation."

This test shows that the *Ixora parviflora* leaf extract of the present invention is not irritating to the eyes.

The above cell model tests and animal safety tests show that the *Ixora parviflora* leaf extract of the present invention has excellent effects of anti-oxidation, inhibiting the activity of matrix metalloproteinase, inhibiting the expression of matrix metalloproteinase, and/or promoting the expression of collagen. Furthermore, the extract is not toxic and irritating, and thus can achieve the effects of improving, repairing, and/or caring for skin without injuring the human body or animal.

The above disclosure is related to the detailed technical contents and inventive features thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered in the following claims as appended.

What is claimed is:

1. A method for anti-oxidation, inhibiting the activity of matrix metalloproteinase (MMP), inhibiting the expression of matrix metalloproteinase, and/or promoting the expression of collagen in a mammal, comprising administering a medicament comprising an effective amount of an *Ixora parviflora* leaf extract to a mammal in need of at least one of the following: anti-aging, anti-photoaging, reducing skin wrinkles, and improving skin flaccidity caused by collagen decomposition, wherein the content of the *Ixora parviflora* leaf extract in the medicament ranges from about 0.03 wt % to about 0.4 wt % based on the total weight of the medicament.

2. The method as claimed in claim 1, wherein the absorption spectroscopy of the extract includes peaks within the following wavelength ranges: from 210 to 250 nm, from 260 to 290 nm, and from 300 to 350 nm.

3. The method as claimed in claim 1, wherein the absorption spectroscopy of the extract includes peaks within the following wavelength ranges: from 220 to 250 nm, from 270 to 290 nm, from 310 to 340 nm, from 390 to 420 nm, and from 650 to 670 nm.

4. The method as claimed in claim 1, wherein the extract is prepared by the following steps: a) extracting *Ixora parviflora* leaves with a polar solvent and collecting the liquid phase; and b) drying the collected liquid optionally, wherein the polar solvent is selected from a group consisting of water, $C_1$-$C_4$ alcohols, and combinations thereof.

5. The method as claimed in claim 4, wherein the polar solvent is selected from a group consisting of water, methanol, ethanol, propanol, butanol, propylene glycol, and combinations thereof.

6. The method as claimed in claim 4, wherein the polar solvent is methanol.

7. The method as claimed in claim 4, comprising, prior to step b), repeating step a) one or more times and combining all the liquid phase to provide the collected liquid for step b).

8. The method as claimed in claim 1, wherein the matrix metalloproteinase is selected from a group consisting of matrix metalloproteinase-1 (MMP-1), matrix metalloproteinase-3 (MMP-3), matrix metalloproteinase-9 (MMP-9), and combinations thereof.

9. The method as claimed in claim 1, wherein the collagen is Type I collagen.

10. The method as claimed in claim 1, which is for improving, repairing, and/or caring for skin.

11. The method as claimed in claim 1, which is for anti-photoaging.

12. The method as claimed in claim 11, which is for anti-photoaging induced by ultraviolet ray B (UVB).

* * * * *